United States Patent [19]
Van Der Puy

[11] Patent Number: 5,654,473
[45] Date of Patent: Aug. 5, 1997

[54] INTERMEDIATES FOR THE SYNTHESIS OF TRIFLUOROMETHYLATED ORGANIC COMPOUNDS

[75] Inventor: Michael Van Der Puy, Erie, N.Y.

[73] Assignee: AlliedSignal Inc., Morris County, N.J.

[21] Appl. No.: 405,312

[22] Filed: Mar. 16, 1995

[51] Int. Cl.$^6$ .......................... C07C 67/02; C07C 33/42
[52] U.S. Cl. .................... 560/262; 568/843; 568/845; 568/849; 570/135; 570/137
[58] Field of Search .................... 560/262; 568/843, 568/845, 849; 570/135, 137

[56] References Cited

U.S. PATENT DOCUMENTS

| | | | |
|---|---|---|---|
| 2,554,533 | 5/1951 | Ladd | 560/262 |
| 5,446,217 | 8/1995 | Van Der Puy | 570/156 |

FOREIGN PATENT DOCUMENTS

| | | |
|---|---|---|
| 62-28032 | 10/1987 | Japan . |
| 62-228032 | 10/1987 | Japan . |

OTHER PUBLICATIONS

Bull. Chem. Soc. Jpn., vol. 60, Fujita et al., "Practical, Sterecontrolled Synthesis of Polyfluorinated Artificial Pyrethroids", Dec. 1987, pp. 4385–4394.
Bull. Chem. Soc. Jpn., vol. 62, Hiyama et al., "A Facile and Practical Synthesis of 1–Aryl–3,3,3–trifluoropropynes", 1989, pp. 1352–1354.
Tetrahedron Letters, vol. 33, No. 4, Jiang et al., "Palladium–Catalyzed Cross–Coupling of . . . Trifluoromethylated 1,3–Dienes", 1992, pp. 511–514.
Piccardi et al., The Peroxide . . . 2–Methylpropene, J. of the Chem. Soc. Perkin Trans. 1, pp. 1146–1149 Jul. 1972.
Rondarev et al., NMR study . . . poly(dluoro–1,3–alkadienes), Zh. Org. Khim., vol. 11(5), pp. 937–943 1975.
Davis et al., Properties of the Halogens, Principles of Chemistry, p. 700 1938.

M. Van Der Puy et al., Journal of Fluorine Chemistry 76 (1996) 49–54. "Preparation, fluorination and synthetic utility of a CFC–olefin adduct".
André J. Laurent et al. "Synthesis of Trifluoromethylalkenes and Alkynes. Trifluoromethyl Captodative Olefins." Tetrahedron Letters, vol. 32, No. 26, pp. 3071–3074 (1991).
Makoto Fujita et al. "Practical Stereocontrolled Synthesis of Polyfluorinated Artificial Pyrethroids." Bull. Chem. Soc. Jpn., 60, 4385–4394 (1987).
Tamejiro Hiyama et al. "A Facile and Practical Synthesis of 1–Aryl–3,3,3–Trifluoropropynes." Bull. Chem. Soc. Jpn., 62, 1352–1354 (1989).
Biao Jiang et al. "Palladium–Catalyzed Cross–Coupling of Trilfluoroisoprpenylzinc Reagent with Vinyl Halides. A Novel Stereospecific Synthesis of Trifluoromethylated 1,3–Dienes." Tetrahedron Letters, vol. 33, No. 4, pp. 511–514 (1992).
Fuqiang Jin et al. "Trifluoroacetyltriphenylsilane as a Potentially Useful Fluorine–Containing Building Block. Preparation and its Transformation into 2,2–Difluoro Enol Silyl Ethers." Tetrahedron Letters. vol. 33, No. 9, pp. 1221–1224 (1992).
Célal Ates et al. "Trifluoroethylidenation of Compounds with Activated Methylene Groups". Tetrahedron Letters. vol. 34, No. 36, pp. 5711–5714 (1993).
Umemoto et al. "New Method of Trifluoromethylation of Enolate Anions and Applications to Regio–, Diasterio–and Enantioselective Trifluoromethylation." J. Org. Chem. vol. 59, No. 19, 5692–5699 (1994).

Primary Examiner—Jose G. Dees
Assistant Examiner—Rosalynd Williams
Attorney, Agent, or Firm—Lois A. Gianneschi

[57] ABSTRACT

Novel trifluoromethylated intermediates are provided which are useful in synthesizing trifluoromethylated organic compounds. Specifically, compounds of the formula $CF_3CCl=CHCH_2X$ are provided, which compounds are versatile intermediates for the synthesis of a wide variety of trifluoromethylated organic compounds.

2 Claims, No Drawings

INTERMEDIATES FOR THE SYNTHESIS OF TRIFLUOROMETHYLATED ORGANIC COMPOUNDS

FIELD OF THE INVENTION

The present invention relates to novel trifluoromethylated intermediates useful in the synthesis of trifluoromethylated organic compounds and, in particular, to 1,1,1-trifluoro-2-chlorobut-2-ene and its derivatives.

BACKGROUND OF THE INVENTION

Fluorinated organic compounds, specifically trifluoromethylated organic compounds, have found great utility as pharmaceuticals, agricultural chemicals, and materials such as liquid crystals. One major route for the synthesis of these organofluorine compounds utilizes trifluoromethylated intermediates.

A number of such trifluoromethylated intermediates and processes for their synthesis have been disclosed. For example, Fujita et al., "Practical Stereocontrolled Synthesis of Polyfluorinated Artificial Pyrethroids", 60 *Bull. Chem. Soc. Jpn.* 4385 (1987) disclose the transformation of a CHO group to CH=C(Cl)CF$_3$ by addition of $^-$CCl$_2$CF$_3$ to an aldehyde carbonyl followed by β-elimination reduction.

Hiyama et at., "A Facile and Practical Synthesis of 1-Aryl-3,3,3-Trifluoropropynes", 62 *Bull. Chem. Soc. Jpn.* 352 (1989) disclose a one-pot reaction by which aldehydes are converted to trifluoromethyl olefins using 1,1,1-trichloro-2,2,2-trifluoroethane, zinc powder, and acetic anhydride.

Laurent et at., "Synthesis of Trifluoromethylalkenes and Alkynes. Trifluormethyl Captodative Olefins", 32 *Tetrahedron Letters* 307 (1991) disclose the preparation of β-ethylthio-β-trifluoromethylketones and aldehydes from β-chloroolefins and ClCF$_3$C=CR$^2$CHO where R$^2$ is phenyl, thienyl, p-chloro-phenyl, or carboethoxy.

Despite the aforementioned disclosures, there exists a continuing need for the development of versatile intermediates from which trifluoromethylated organic compounds may be prepared.

SUMMARY OF THE INVENTION

The present invention provides trifluoromethylated compounds of the general formula:

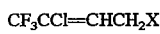

CF$_3$CCl=CHCH$_2$X wherein X is hydrogen, fluorine, bromine, iodine, OC(O)CH$_3$, or hydroxyl. The compounds of the present invention are particularly useful and versatile intermediates for the synthesis of organofluorine compounds because they contain a trifluoromethyl group, a reactive allylic X group, and a CCl=CH group which is a latent, or masked, carbonyl group. The presence of these groups provides the intermediates of the present invention with ample functionality for their further chemical transformation.

DESCRIPTION OF THE PREFERRED EMBODIMENTS

The trifluoromethylated compounds of the present invention are of the general formula:

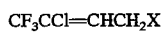

CF$_3$CCl=CHCH$_2$X wherein X is hydrogen, fluorine, bromine, iodine, OC(O)CH$_3$, or hydroxyl. Preparation of the compounds of the present invention proceeds by the general reaction:

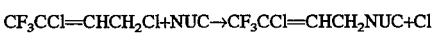

CF$_3$CCl=CHCH$_2$Cl+NUC→CF$_3$CCl=CHCH$_2$NUC+Cl wherein NUC represents the nucleophile.

The starting material for the reaction, 1,1,1-trifluoro-2,4-dichlorobut-2-ene, or HCFC-1343, may be prepared by passing HCFC-353, or 1,3,3-trichloro-4,4,4-trifluorobutane, over a catalyst at a temperature of about 285° C. Specifically, the catalyst is charged to a reactor, heated to 285° C. under a nitrogen flow, and HCFC-353 is fed into the reactor. Contact times are from about 1 second to about 60 seconds, preferably from about 5 seconds to about 20 seconds. Pressure is not critical. Conversions for this process are approximately 50%.

HCFC-353 may be produced by an addition reaction of ethylene and 1,1,1-trichloro-3,3,3-trifluoropropane, which are commercially available from AlliedSignal Inc. and other domestic chemical manufacturers. Any commercially available catalyst known in the art to be useful in catalyzing the addition of halocarbons to olefins may be employed. Suitable addition catalysts include, without limitation, Copper (I) salts such as cuprous chloride and cuprous iodide, iron (II) salts such as ferrous chloride and ferrous acetate, and metal carbonyls such as iron carbonyl and cobalt carbonyl. Cuprous chloride is preferred. Optionally, any well known co-catalyst useful in catalyzing the addition of halocarbons to olefins may be employed in the reaction. Suitable addition co-catalysts include aliphatic or aromatic amines such as pyridine and diethylamine.

Any inert solvent which can dissolve the catalyst and is miscible with the halocarbon may be used in the reaction. Suitable solvents include, without limitation, commercially available low molecular weight nitriles such as acetonitrile and propionitrile, low molecular weight alcohols such as tertiary butanol and isopropanol, and amides such as dimethylformamide. Acetonitrile is preferred because of ease of handling and stability.

The temperature at which the addition reaction is conducted and the period of reaction will depend upon the catalyst used. One of ordinary skill in the art can readily optimize the conditions of the reaction without undue experimentation to produce HCFC-353, but the temperature will generally be in the range of from about 50° to about 150° C. for a period of from about 8 to about 72 hours.

Pressure is not critical. Preferably, the reaction is conducted in an apparatus made of corrosion resistant material such as TEFLON® and glass. The addition product, HCFC-353, may be recovered by any means well known in the art such as distillation and extraction.

The HCFC-353 is used to prepare HCFC-1343 as outlined in general above. Useful catalysts for the preparation of HCFC-1343 include, without limitation, metal oxides such as chrome (III) oxide, supported metal oxides such as chrome (III) oxide supported on aluminum oxide or carbon, and supported metal halides such as cobalt (II) chloride and nickel (II) chloride supported on carbon, aluminum oxide, aluminum fluoride, or a mixture of such supported materials, such as a mixture of Cr$_2$O$_3$ and Al$_2$O$_3$. Chrome (III) oxide is preferred due to its level of reactivity and commercial availability. Suitable chrome (III) oxide catalysts are available from Mallinckrodt Specialty Chemicals Co., St. Louis, Mo. One of ordinary skill in the art can readily optimize the conditions of the reaction, without undue experimentation, to obtain the HCFC-1343 byproduct. Pressure is not critical.

The trifluoromethylated intermediates of the present invention are prepared using HCFC-1343 in either a one or a two step reaction. In general, the HCFC-1343 and the nucleophile are dissolved in a solvent and reacted. Any inert solvent miscible with the halocarbon and nucleophile may be used. Exemplary solvents are, without limitation, low molecular weight alcohols such as methanol and ethanol, amides such as dimethylformamide, ketones such as acetone, sulfolane, and dimethylsulfoxide. Preferably, the solvent is methanol, acetone, or dimethylformamide which are inexpensive, readily available solvents.

Reactions of the type utilized for the production of the claimed trifluoromethylated intermediates of the present invention are known. Further, reaction conditions for the production of the claimed intermediates can be readily determined by one of ordinary skill in the art. The conditions will depend upon the nucleophile and solvent utilized. In general, the HCFC-1343 and nucleophile are reacted at a temperature from about 25° C. to about 150° C. or the boiling point of the solvent The period of reaction is from about several minutes to about several days. The pressure at which the reaction is carried out is, generally, not critical.

The iodide intermediate of the present invention may be prepared by refluxing a mixture of sodium iodide and HCFC-1343 in an at least 1:1 molar equivalent ratio in a solvent. The preferred solvent is acetone because sodium iodide is appreciably soluble, and the byproduct sodium chloride appreciably insoluble, in acetone.

Preparation of the bromide intermediate proceeds in a fashion similar to that of the iodide intermediate. A mixture of sodium bromide and HCFC-1343 are refluxed in a solvent. However, because the solubility of both sodium bromide and the byproduct sodium chloride in the preferred solvent, acetone, are comparable an excess of sodium bromide, from about 1.2 to about 2.0 equivalents, must be used in conjunction with a longer reaction time in order to achieve high conversions.

The fluoride intermediate may be prepared by heating a metal fluoride, such as sodium fluoride, cesium fluoride, or preferably potassium fluoride with HCFC-1343 in a solvent having a boiling point of about 50° C. to about 250° C. Reaction times will vary depending on the solvent and are best determined by analysis during the course of the reaction. At least 1 molar equivalent of metal fluoride is used. Suitable solvents include polar, aprotic solvents such as dimethylsulfoxide, sulfolane, and, preferably, dimethylformamide.

For the preparation of the acetate intermediate, either sodium acetate or potassium acetate may be mixed with HCFC-1343 in a solvent and heated until the desired conversion is attained. The solvent used may be a low molecular weight alcohol or dimethylformamide. Dimethylformamide is preferred because the reaction times are considerably less when this solvent is utilized. If dimethylformamide is used as a solvent, an aqueous work-up is used to remove solvent and inorganic salts from the product prior to distillation.

The preparation of the alcohol intermediate may proceed by hydrolysis of the acetate intermediate using potassium hydroxide or sodium hydroxide in a solvent, preferably methanol or a mixture of methanol and water. The reaction proceeds quickly and is exothermic and, thus, cooling may be necessary to control the reaction. Reaction times are about one hour or less at a temperature of about 35° C. Alternatively, the alcohol intermediate may be prepared from the HCFC-1343 in a one-pot reaction in which the HCFC-1343 is refluxed with sodium acetate or potassium acetate in methanol or ethanol.

The 1,1,1-trifluoro-2-chlorobut-2-ene intermediate may be prepared by the catalytic reduction of the alcohol intermediate in the absence of base. Well known catalysts, such as supported rhodium or palladium, preferably Rh/C, and relatively mild conditions, i.e., hydrogen pressures from about 1 to about 10 atm. and temperatures from about 30° C. to about 150° C. may be used. Alternatively, the Grignard reagent of the bromide or iodide intermediate may be treated with a proton source, such as an aqueous acid, to produce the 1,1,1-trifluoro-2-chlorobut-2-ene. As yet another alternative, the bromide or, preferably, the iodide intermediate may be selectively reduced with a reducing agent.

The resulting intermediate compounds of the present invention are liquids which may be purified by distillation. The ratio of the geometrical isomers for these compounds is the same as that for HCFC-1343, which is about 93–97% Z-isomer to about 3–7% E-isomer.

One of ordinary skill in the art will recognize that the trifluoromethylated compounds of the present invention are useful as intermediates for the preparation of a wide variety of organofluorine compounds. Exemplary of such organofluorine compounds are, without limitation, trifluoromethylated alcohols, alkynes, aldehydes, esters, amines, and sulfur compounds. Such trifluoromethylated organic compounds are used in or as pharmaceuticals, agricultural chemicals, and liquid crystals.

Alternatively, the compounds of the present invention may be used for the preparation of other intermediates such as $CF_3CCl=CHCHO$, $CF_3CCl=CHCH_2CN$, $CF_3CCl=CHCH_2SCH_3$, $CF_3CCl=CHCH_2N(Et)_2$, $CF_3CH_2CH_2CH_2OH$, $CF_3CCl=CHCH_2CH(COOR)_2$, $CF_3CCl=CHCOOR$, and $CF_3CCl=CHCH_2NH_2$ wherein R is alkyl or aryl. These intermediates also are useful in synthesizing trifluoromethylated organic compounds.

The versatility of the intermediates of the present invention will be readily apparent to those ordinarily skilled in the art. As an example, one intermediate of the present invention, 3-chloro-4,4,4-trifluorobut-2-en-1-ol may be reduced in the presence of a base to 4,4,4-trifluorobutan-1-ol which is used in pharmaceuticals. Alternatively, reduction of 3-chloro-4,4,4-trifluorobut-2-en-1-ol without base results in 1,1,1-trifluoro-2-chlorobut-2-ene, a precursor to the dienophile 1,1,1- trifluorobut-2-yne. As yet another example, the alcohol intermediate may be oxidized to the aldehyde which is used in the preparation of insecticides.

The intermediates of the present invention, their preparation and use will be clarified further by a consideration of the following examples.

EXAMPLE 1

A 600 mL stirred Monel autoclave was charged with 30 mL $CH_3CN$, 3 mL pyridine, 1 g. CuI, and 199.6 g. $CF_3CCl_3$. The contents were cooled to −29° C., the autoclave briefly evacuated, and charged with 24.4 g. ethylene. The contents were heated to 135°–145° C. for 22 h. After cooling the contents, the volatiles (unreacted ethylene) were vented. The residue was diluted with 300 mL water and extracted with 50 mL $CH_2Cl_2$. The organic layer was washed twice with 50 mL 5% aqueous HCl,2×50 mL 5% NaOH,2×50 mL water and dried with $CaCl_2$. Distillation at 145 mm Hg gave 80 g., 58% yield, of a colorless liquid identified spectroscopically as HCFC353, b.p. 102°–103° C. $^1$H NMR: equal intensity triplets at δ3.9 and2.77. $^{19}$F NMR: −81 (s) ppm. IR: strong bands characteristic of $CF_3CCl_2CH_2$—grouping at 1255, 1210, and 1180 $cm^{-1}$. Gas chromatography ("GC") determined that the product was 99% pure.

EXAMPLE 2

A Monel tube reactor was charged with 250 cc. of ⅛ in. $Cr_2O_3$ pellets and heated to 285° C. under a nitrogen flow.

747 g. HCFC-353 was fed into the reactor at 40 mL/h. and nitrogen at 10 cc/min. 643 g. of organic products were collected in cold traps and consisted of 37% $CF_3CCl=CHCH_2Cl$, HCFC-1343, and 62% starting material by GC analysis. This indicated a 38% conversion and 97% selectivity for HCFC-1343. Distillation provided pure product with a 101° C. b.p.

EXAMPLE 3

Potassium acetate, 40.0 g., 0.41 mol, were added to a solution of 60.0 g., 0.335 mol, $CF_3CCl=CHCH_2Cl$ in 100 mL dimethylformamide and the mixture stirred and heated under nitrogen to 75° C. for 10 minutes. The cooled reaction mixture was poured into 200 mL water and extracted with 2×75 mL ether. The combined organic layers were washed with 3×50 mL. water and dried with $Na_2SO_4$. Distillation gave 53.9 g., 0.266 mol, 79% yield of (3-chloro-4,4,4-trifluorobut-2-enyl) acetate, b.p.43°–45° C. at 10 mm Hg. GC indicated a mixture of geometrical isomers in a 93:7 ratio. FT-IR, thin film: 3069, 2943, 1752, 1675, 1436, 1382, 1367, 1307, 1227, 1190, 1148, 1050, 933, 813, and 735 $cm^{-1}$. $^1H$ NMR: major isomer, δ2.09 (s, 3 H), 4.82 (dq, J=5.8 and 2.0 Hz), 6.58 (tq, J=5.8 and 1.0 Hz); minor isomer, 2.08 (s), 4.8 (hidden), and 6.30 (t, J=6.2 Hz).$^{19}F$ NMR: major isomer, −70.3 ppm; minor isomer, −64.4 ppm. IR: 1752 $cm^{-1}$(C=O) and 1674 $cm^{-1}$(C=C).

EXAMPLE 4

A solution of 80 g. NaOH in 30 mL water was added, over 1 hour, to 40.6 g. of the (3-chloro4,4,4-trifluorobut-2-enyl) acetate of Example 2 in 40 mL methanol, keeping the temperature less than 35° C. with the use of a water bath. After 1 hour, the mixture was diluted with 100 mL water. The lower layer was separated and the aqueous layer extracted with 2×50 mL ether. The combined organic layers were washed with 25 mL brine, dried with $Na_2SO_4$, and distilled to give 26.9 g., 84% yield, of 99.7% pure, by GC, 3-chloro-4,4,4-trifluorobut-2-en-1-ol, b.p. 55° C. at 18 mm Hg. $^1H$ NMR: δ6.59 (t, 1 H), 4.39 (dq, 2 H), and 3.69 (s, 1 H). $^{19}F$ NMR: −70.1 ppm. IR: 3340 $cm^{-1}$ (OH) and 1669 $cm^{-1}$ (C=C).

EXAMPLE 5

A mixture of potassium acetate, 122 g., 1.24 mol, methanol 600 mL, and 195.2 g., 1.09 mol $CF_3CCl=CHCH_2Cl$ were refluxed under nitrogen for 48 h. Sodium hydroxide, 6.0 g., were added and reflux continued for 2 h. The bulk of the methanol was distilled and the cooled residue treated with 200 mL water. The aqueous mixture was extracted with 2×50 mL ether, washed with brine and dried. Distillation at 17–18 mm Hg gave 128.2 g., 73% yield, of colorless 3-chloro-4,4,4-trifluorobut-2-en-1-ol, b.p.54°–55° C. of 99% purity.

EXAMPLE 6

To a solution of 30.0 g., 0.1 mol NaI in 150 mL acetone at room temperature were added 36.0 g., 0.20 mol, $CF_3CCl=CHCH_2Cl$. The mixture was stirred for 4 h. and filtered. The filter cake was washed with a small amount of acetone and the filtrate concentrated by rotary evaporation. The concentrate was washed with 40 mL 10% aq. sodium sulfite, dried with $MgSO_4$, and distilled at 52 mm Hg. 40.7 g., 75% yield, of a yellow oil were obtained and identified as 1-iodo-3-chloro-4,4,4-trifluorobut-2-ene, b.p. 68° C. $^1H$ NMR: δ6.74 (t, 1 H) and 3.97 (dq, 2 H). $^{19}F$ NMR: −70.0 ppm. IR: 1650 $cm^{-1}$ (C=C).

EXAMPLE 7

Sodium bromide, 25.0 g., 0.24 mol, $CF_3CCl=CHCH_2Cl$, 35.6 g., 0.199 mol, and 150 mL acetone were refluxed for 21 h., cooled and filtered. The filtrate and 11.0 g. fresh NaBr were then refluxed for an additional 3 days. After cooling and filtering the mixture, the filtrate was distilled to give 36.7 g., 82% yield, of 95% pure 1-bromo-3-chloro-4,4,4-trifluorobut-2-ene as a 93.4:6.6 mixture of isomers, b.p. 117°–122° C. $^1H$ NMR: δ6.71 (t, J=8 Hz, 1 H), 4.04 (d, J=8 Hz, 2 H). $^{19}F$ NMR: major isomer, −70.0 ppm and minor isomer −63.0 ppm. IR: 1657 $cm^{-1}$ (C=C).

EXAMPLE 8

Potassium fluoride, 9.0 g., dimethylformamide 50 mL and 20.2 g. $CF_3CCl=CHCH_2Cl$ were heated under nitrogen reflux in a flask fitted with a distillation column and take-off head. Volatiles were removed up to a head temperature of 100° C. over a period of 3 h. The crude material was redistilled to give 1,1,1,4-tetrafluoro-2-chlorobut-2-ene, b.p. 65° C. $^1H$ NMR: δ6.7 (dt, J=13.9 and 5.3 Hz, 1 H) and 5.2 (ddq, J=46.3, 5.3 and 2 Hz, 2 H). $^{19}F$ NMR: −70.5 and −224.4 ppm (td, J=46.3 and 13.9 Hz).

EXAMPLE 9

Hydrogenation of 18.8 g. of 3-chloro-4,4,4-trifluorobut-2-en-1-ol was conducted at a pressure of 45 psig and 75° C. using 0.160 g. 5% Rh/C as catalyst. Approximately one equivalent of $H_2$ was taken up in 24 h. The mixture was cooled and centrifuged. Analysis of the lower liquid layer, 13.8 g., indicated essentially complete conversion of starting material. Distillation gave 8.2 g., b.p. 56°–57° C. of a colorless liquid identified as a Z-isomer/E-isomer mixture of 1,1,1-trifluoro-2-chlorobut-2-ene, 98.5% purity and 49% yield. Mass spectroscopy (m/z, %):39 (35.6); 75 (100); 77 (31.7); 89 (28.8); 144 (P, 65); 146 (P+2, 19.4). $^{19}F$ NMR:−69.8 ppm. $^1H$ NMR:δ1.88 ( 3 H, dq, J=6.8 and 2.23 Hz), 6.55 (1 H, qq, J=6.8 and 1.0 Hz).

EXAMPLE 10

A 375 mL pressure bottle was charged with 16.1 g., 0.10 mol of 3-chloro-4,4,4-trifluorobut-2-en-1-ol, 9.8 g., 0.10 mol potassium acetate, 30 mL methanol and 55 mg. 5% Pd/C catalyst. Hydrogenation was carried out at 45°–50° C. and an operating pressure at 40–60 psig, adding $H_2$ as needed until the theoretical quantity had been taken up, about 14 h. The mixture was cooled and filtered and the filtrate poured into 150 mL water and extracted 4×50 mL ether. The combined ether layers were washed with 50 mL bicarbonate solution, 50 mL brine, and dried with $MgSO_4$. Distillation gave 9.4 g., 73% yield, of 97% pure 4,4,4-trifluorobutan-1-ol.

Other embodiments of this invention will be apparent to those skilled in the art from a consideration of this specification or practice of the invention herein.

What is claimed is:
1. A compound which is (3-chloro-4,4,4-trifluorobut-2-enyl) acetate.
2. A compound which is 3-chloro-4,4,4-trifluorobut-2-en-1-ol.

* * * * *

UNITED STATES PATENT AND TRADEMARK OFFICE
CERTIFICATE OF CORRECTION

PATENT NO : 5,654,473
DATED : August 5, 1997
INVENTOR(S) : Van Der Puy et al.

It is certified that error appears in the above-identified patent and that said Letters Patent is hereby corrected as shown below:

Column 3, line 20, delete "solvent", and substitute -- solvent. -- therefor.

Column 4, line 59, delete "HCFC353" and substitute -- HCFC-353 -- therefor.

Column 5, line 30, delete "80" and substitute -- 8.0 -- therefor.

Column 5, line 31, delete "3-chloro4,4,4-" and substitute -- 3-chloro-4,4,4 -- therefor.

Signed and Sealed this

Eighth Day of February, 2000

Q. TODD DICKINSON

Attest:

Attesting Officer

Commissioner of Patents and Trademarks